US006767535B1

(12) United States Patent
Rollins et al.

(10) Patent No.: US 6,767,535 B1
(45) Date of Patent: Jul. 27, 2004

(54) SUPPRESSING TUMOR FORMATION USING CELLS EXPRESSING JE/MONOCYTE CHEMOATTRACTANT PROTEIN-1

(75) Inventors: Barrett Rollins, Brookline, MA (US); Charles Stiles, Newton Center, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 08/453,347

(22) Filed: May 30, 1995

Related U.S. Application Data

(63) Continuation of application No. 08/003,136, filed on Jan. 12, 1993, now abandoned, which is a continuation-in-part of application No. 07/701,515, filed on May 16, 1991, now Pat. No. 5,179,078, which is a continuation-in-part of application No. 07/351,008, filed on May 12, 1989, now Pat. No. 5,212,073.

(51) Int. Cl.$^7$ .................. A06N 63/99; A61K 48/00; C12N 15/00

(52) U.S. Cl. .............. 424/93.21; 424/93.2; 435/325

(58) Field of Search .................... 424/93–2, 21, 424/93 B; 435/325, 320.1, 240.2, 135.1, 172.3, 252.3, 69.5; 514/44, 2, 8, 12; 530/324, 350, 351; 935/62

(56) References Cited

U.S. PATENT DOCUMENTS

| | | | | |
|---|---|---|---|---|
| 4,399,216 | A | 8/1983 | Axel et al. .................. | 435/6 |
| 4,477,571 | A | 10/1984 | Chang et al. ................ | 435/253 |
| 5,179,078 | A | * 1/1993 | Rollins et al. .................. | 514/2 |
| 5,212,073 | A | 5/1993 | Rollins et al. ............. | 435/69.5 |
| 5,278,287 | A | 1/1994 | Rollins et al. ............... | 530/351 |

FOREIGN PATENT DOCUMENTS

| | | |
|---|---|---|
| WO | 90/07863 | 7/1990 |
| WO | 90/08777 | 8/1990 |
| WO | 90/08778 | 8/1990 |

OTHER PUBLICATIONS

Crystal (1995) Science 270, 404–410.*
Vieweg et al (1995) Cancer Invest. 13, 193–201.*
Anderson (Sep. 1995) Scientific American 124–128.*
Blau et al (Nov. 2, 1995) New Eng. J. Med. 1204–1207.*
Marchall, Science 269:1050–1055, 1995.*
LaFont et al., Lancet, 346 : 1442–1443, 1995.*
Orkin et al., NIH "Repoit and Recommendations . . . " Dec. 7, 1995, 1–40.*
Rosenberg et al, N. Eng. J. Med, vol. 323 No. 9, pp 510–57 Aug. 30, 1990.*
Bottazzi et al, Cytokine, vol. 3(5), p. 519, 1991.*
Yamaue et al., Nippon Gan Chiryo Gakkai Shi, vol. 25(5) pp. 978–989 (May 20, 1990).*
Yasuji Furutani et al., "Cloning and sequencing of the cDNA for human monocyte chemotactic and activating factor (MCAF)," *Biochemical and Biophysical Reswearch Communications*, 159(1):249–255 (1989).
Rollins, Barrett J. et al., "A Cell–Cycle Constraint on the Regulation of Gene Expression by Platelet–Derived Growth Factor," *Science*, 238:1269–1271, (1987).
Rittling, Susan R. et al.,, "Expression of Cell cycle–dependnet genes in young and senescent WI–38 fibroblasts," *Proc. Natl. Acad. Sci. USA*, 83:3316–3320, (1986).
Cochran, Brent H. et al., "Molecular Cloning of Gene Sequences Regulated by Platelet–derived Growth Factor," *Cell*, 33:939–947, (1983).
Yoshimura, Teizo et al., "Human monocyte chemoattractant protein–1 MCP–1)," *FEBS Letters*, 244 (2):487–493, (1989).
Zachariae, Claus O.C. et al., "Properties of monocyte chemotactic and activating factor (MCAF) purified from a human fibreosarcoma cell line," Brief Definitive Report, *The Journal of Experimental Medicien*, 171:2177–2182 (1990).
Graves, D.T. et al., "Identification of Monocyte Chemotactic Activity Produced by Malignant Cells," *Science*, 245:1490–1491, (1989).
Valente, Anthony J. et al., "Purification of a Monocyte Chemotactic factor Secreted by Nonhuman Primate Vascular Cells in Culture," *Biochemistry*, 27:4162–4168 (1988).
Rollins, Barrett J. and Sunday, Mary E., "Suppression of Tumor Formation In Vivo by Expression of the JE Gene in Malignant Cells", *Molecular and Cellular Biology*, 11(6):3125–3131 (1991).
Robinson, Elizabeth A. et al., "Complete amino acid sequence of a human monocyte chemoattractant, a putative mediator of cellular immune reactions", *Proc. Natl. Acad. Sci.USA*, 86:1850–1854, (1989).
Rollins et al., "The Human Homolog of the JE Gene Encodes a Monocyte Secretory Protein," *Molecular and Cellular Biology*, 9(11):4687–4695, (1989).
Bottazzi et al., "Monocyte Chemotactic Cytokine Gene Transfer Modulates Macrophage Infiltration, Growth and Susceptibility to IL–2 Therapy of a Murine Melanoma," *Journal of Immunology* 148: 1280–1285 (1992).
Yoshimura et al., "Purification and Amino Acid Analysis of Two Human Glioma–DerivedMonocyte Chemoattractantas," *Journal of Experimental Medicine* 169: 1449–1459 (1989).
Matsushima et al., "Purification and Characterization of a Novel Monocyte Chemotactic and Activating Factor Produced by a Human Myelomonocytic Cell Line," *Journl of Experimental Medicine* 169: 1485–1490 (1989).

(List continued on next page.)

*Primary Examiner*—Deborah Crouch
(74) *Attorney, Agent, or Firm*—Hamilton, Brook, Smith and Reynolds, P.C.

(57) ABSTRACT

A method of suppressing tumor formation in a vertebrate by administering JE/MCP-1 is described. Also described are methods of treating localized complications of malignancies and methods of combatting parasitic infection by administering JE/MCP-1.

3 Claims, 4 Drawing Sheets

OTHER PUBLICATIONS

Graves et al., "Identification of Monocyte Chemotactic Activity Produced by Malignant Cells", *Science 245*: 1490–1493 (1989).

Valente et al., "Purification of a Monocyte Chemotactic Factor Secreted by Nonhuman primate Vascular Cells in Culture", *Biochemistry 27*: 4162–4168 (1988).

Zachariae et al., "Properties of Monocyte Chemotactic and Activating Factor (MCAF) Purified from a Human Febrosarcoma Cell Line," *Journal of Experimental Medicien 171*: 2177–2182 (1990).

* cited by examiner

SUPPRESSING TUMOR FORMATION USING CELLS EXPRESSING JE/MONOCYTE CHEMOATTRACTANT PROTEIN-1

RELATED APPLICATION

This application is a continuation of application Ser. No. 08/003,136 filed on Jan. 12, 1993 now abandon, which in a Continuation-in-Part of Ser. No. 07/701,515 filed May 16, 1991 now U.S. Pat. No. 5,179,078 which is a CIP of Ser. No. 07/351,008 filed May 2, 1989 now U.S. Pat. No 5,212,073.

GOVERNMENT SUPPORT

The invention described herein was supported in whole or in part by grants from the National Institute of Health.

BACKGROUND

Cancer results when a vertebrate's own cells become malignant. Healthy individuals at any given time carry potentially malignant cells in their body. These cells are generally recognized and killed by the individuals' immune system. However, some malignant cells are not destroyed by the immune system and proliferate into tumors.

Currently, there are not adequate and specific therapies for cancer. For example, surgical excision of tumors is not an effective method of treatment where the cancer has metastasized. In addition, radiation and chemotherapy often kill normal cells in addition to cancerous cells.

Another problem is that chemotherapeutic agents follow first-order kinetics. As a result, a constant percentage, rather than a constant number of cells are killed by a given application of a chemotherapeutic agent. Consequently, malignant cells, which could cause a relapse in the disease, remain even when a patent is diagnosed as having complete clinical remission.

A method of suppressing cancer that employs the individual's own immune system would be useful.

SUMMARY OF THE INVENTION

The present invention relates to Applicant's finding that expression of the JE/MCP-1 protein in malignant cells suppresses their ability to form tumors in vivo. Thus, the invention comprises, in one embodiment, a method of suppressing tumor formation in a vertebrate by administering to the vertebrate a therapeutically effective amount of JE/MCP-1. The protein can be administered alone or as an adjuvant to surgery or cytotoxic chemotherapy.

The suppressive effect of JE/MCP-1 depends on the induction of the vertebrate's immune response, specifically the response of monocytes. Thus, in another embodiment, the invention comprises a method of increasing a vertebrate's monocyte-mediated tumoricidal activity in vivo by administering to the vertebrate an effective amount of JE/MCP-1.

JE/MCP-1 can also be administered to treat localized complications of malignancy. For example, JE/MCP-1 could be used to inhibit malignant pleural effusions or ascites. Therefore, in a further embodiment, the invention comprises methods of inhibiting pleural effusion or ascites in a vertebrate by locally administering JE/MCP-1 to the anatomic spaces between the lung and the pleural membrane or the stomach and the peritoneum.

In a further embodiment tumor killing cells, such as tumor infiltrating lymphocytes (TIL cells) are genetically engineered to express the JE/MCP-1 protein. The engineered cells therefore can be administered to a vertebrate to provide a synergistic local tumor cell killing.

In the alternative, any cell type which localizes to, or can be made to localize to a site of tumor formation can be genetically engineered to express JE/MCP-1 protein and used for gene therapy. Cells can be engineered in vivo, at the site of tumor formation, or they can be engineered Ad vitro, and subsequently administered to a vertebrate where they will express JE/MCP-1 at the site of tumor formation.

The presence of JE/MCP-1 in vivo is accompanied by a local increase in the presence of eosinophils. Therefore, another aspect of the subject invention comprises methods of combatting a parasitic infection in a vertebrate animal by administering to that vertebrate an effective amount of JE/MCP-1.

A major advantage of using JE/MCP-1 in treating cancer is that it employs the individual's own immune system and therefore would have fewer side-effects than conventional chemotherapies. In addition, JE/MCP-1 stimulates monocytes and, as such, does not depend on a total immunologic response.

DETAILED DESCRIPTION OF THE INVENTION

Figure 1:
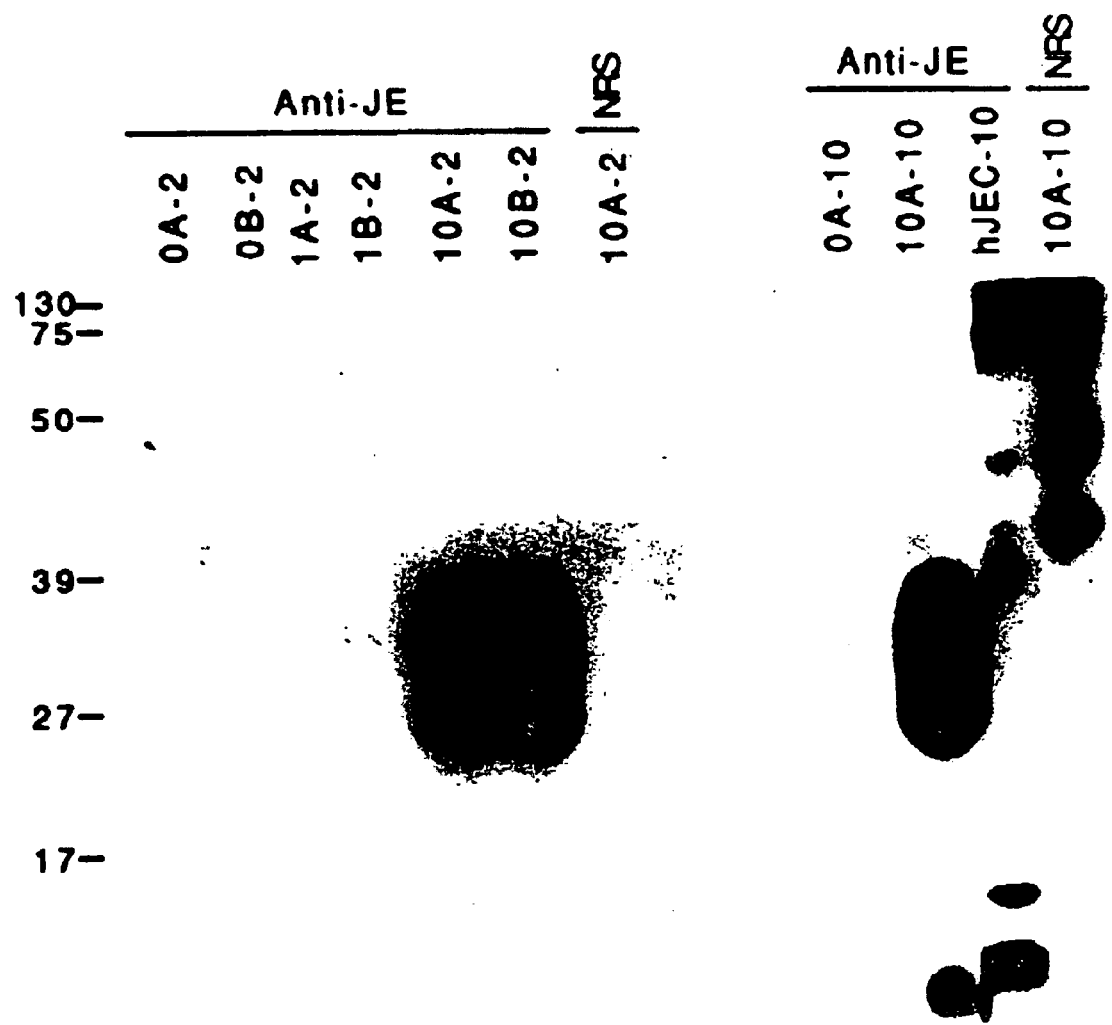
FIG. 1 is an autoradiograph of polyacrylamide gel electrophoresis of cells of DUKX-B11 cells transfected with pXM alone (0A-2, 0B-2, and 0A-10), pXM-JE1 (1A-2 and 1B-2), pXM-JE10 (10A-2, 10 0B-2, and 10A-10), or pXM-hJE34 (hJEC-10 and hJEC-100).

The present invention is based on the finding that expression of the JE/MCP-1 protein in malignant cells suppresses their ability to form tumors in vivo.

The JE gene is a platelet-derived growth factor (PDGF)-inducible "competence" or "early response gene" first identified in mouse 3T3 cells (Cochran, B. H. *Cell* 33:939–947 (1983)). Sequence and expression analysis showed that unlike other early response genes, such as c-myc, c-fos, or c-jun, the murine JE gene encodes a secreted glycoprotein with cytokine-like properties (Kawahara, R. S. *J. Biol. Chem.* 264:679–682 (1989); Rollins, B. J. *Proc. Natl. Acad. Sci. USA* 85:3738–3742 (1988)). The human homolog of murine JE has been cloned, (Rollins, B. J. *Mol. Cell. Biol.*, 9:4687–4695 (1989)), and the predicted amino acid sequence of its protein is identical to that of a monocyte chemoattractant, MCP-1. (Yoshimura, T., *J. Exp. Med.*, 169:1449–1459 (1989) (Yoshimura T. *JE. FEBS Lett.* 244:487–493 (1989)) also called MCAF (Furutani, Y. et al., *Biochem. Biophys. Res. Commun.* 159:249–255 (1989); Matsushima, K. et al., *J. Ex. Med.* 1:1485 1490 (1989) and SMC-CF (Graves, D. T., et al., *Science* 2:1490–1493 (1989); Valente, A. J. et *Biochem* 27:4162–4168 (1988)).

The JE/MCP-1 protein is structurally related to the members of a large, recently identified family of low molecular weight secreted proteins that appear to be involved in the inflammatory response (Leonard, E. J. and T. Yoshimura *Immunol. Today* 11:97 101 (1990); Rollins, B. J. et al., *Mol. Cell. Biol.* 9:4687–4695 (1989); Wolpe, S. D. and A. Cerami, *FASEB J.* 3:2563–2573 (1989)). The genes for many of these proteins, including human JE/MCP-1, are clustered on chromosome 17q11.2–12 (Donlon, T. A. et al., *Genomics* 6:548–553 (1990); Irving, S. G., et al., *Nucleic Acids Res.* 18:3261 3270 (1990); Rollins, B. J., et al., *Genomics* (in press)) or mouse chromosome 11 (Wilson, S. D., et al., *J. Exp. Med.* 171:1301–1314 (1990)). These genes are also related to the genes encoding another family of cytokines, whose members include the neutrophil activator NAP-1/IL-8 (Peveri, P., et al., *J. Exp. Med.* 167:1547–1559 (1988); Schroder, J. M. et al. *J. Immunol* 139:3474–3483 (1987); Yoshimura, T. et al., *Proc. Natl. Acad. Sci. USA* 84:9233–9237 (1987)) many of which cluster at 4q12–21 (Griffin, C. A. et al., *Cytogenet Cell Genet.* 45:67–69 (1987); Luster, A. D. et al. *Proc. Natl. Acad. Sci. USA* 84:2868–2871 (1987); Richmond, A. *EMBO J.* 2:2025–2033 (1988)).

JE/MCP-1 exerts several effects specifically on monocytes. Both natural and recombinant JE/MCP-1 are potent chemoattractants for human monocytes in vitro, (Matsushima, K. et al., *J. Exp. Med.* 169:1485–1490 (1989); Yoshimura, T. et al., *J. Exp. Med.* 169:1449–1459 (1989)) and purified recombinant JE/MCP-1 can stimulate an increase in cytosolic free calcium and the respiratory burst in monocytes (Zachariae, C. O. C., et al., *J. Exp. Med.* 171:2177–2182 (1990); Rollins, B. J. et al., *Blood* (in press)). Purified natural JE/MCP-1 has also been reported to activate monocyte-mediated inhibition of tumor cell growth, but not tumor cell killing, in vitro (Matsushima, K. et al., *J. Exp. Med.* 169:1485–1490 (1989)).

The following demonstrates that expression of the JE gene in malignant cells suppresses their ability to form tumors i vivo. This apparent phenotypic reversion requires interaction with host factors in vivo, since expression of JE/MCP-1 does not alter the transformed character of these cells in vitro. Furthermore, the following shows that JE/MCP-1-expressing cells exert their effect in trans by their ability to suppress tumor formation when co-injected with JE/MCP-1-non-expressing tumor cells.

In order to create malignant cells expressing JE/MCP-1, the DHFR deletion mutant CHO cell line, DUKXB-11 (G. Urlaub and L. A Chasin, *Proc. Natl. Acad. Sci. USA*, 77:4216–4220 (1980)) was transfected with the expression vector pXM (Yang, Y.-C. et al., *Cell* 47:3–10 (1986) containing a variety of JE cDNA species. High levels of JE/MCP-1 protein expression were achieved in stably transfected lines by methotrexate (MTX)-induced DNA amplification. R. J. Kaufman et al., *EMBO J.* 6:187–193 (1987).

FIG. 1 shows JE/MCP-1 protein expression in independently derived cell lines selected for resistance to 2 or 10 $\mu$M MXT. There is no detectable JE/MCP-1 protein secreted from cell lines transfected with pXM alone (cell lines 0A-2 and 0B-2; cell line 0A-10 was derived from 0A-2) or with pXM containing murine JE cDNA in the antisense orientation (1A-2 and 1B-2). Considerable JE/MCP-1 protein was secreted by cell lines transfected with murine JE cDNA in the sense orientation (10A-2 and 10B-2; 10A-10 was derived from 10A-2) and human JE cDNA (hJEC-10). Cell line hJEC-100, derived from hJEC-10 by selecting for resistance to 100 $\mu$M MTX, also secreted human JE/MCP-1 protein.

Murine JE cDNA directs CHO cells to secrete a microheterogeneous protein of $M_r$ 27–39,000, similar to the natural protein and the protein expressed in a COS cell expression system. Rollins, B. J. et al., *Proc. Natl. Acad. Sci. USA* 85:3738–3742 (1988)). Nearly half of the apparent $M_r$ is due to O-linked glycosylation. Human JE/MCP-1 proteins expressed in CHO cells are also similar to native and COS cell expressed JE/MCP-1$\alpha$ ($^M_r$15,000) and JE/MCP 1$\beta$ ($M_r$ 11,000). (Rollins, B. J., et al. *Mol. Cell. Biol.* 9:4687–4695 (1989).

The monocyte chemoattractant activities (MCA) secreted by these cell lines were determined as described in detail in Example 1. They were 1415 U/24 hr/$10^6$ cells (10A-2), 1079 U/24 hr/$10^6$ cells (10B-2), 3008 U/24 hr/$10^6$ cells (10A-10), 54 U/24 hr/$10^6$ cells (hJEC-10), and 692 U/24 hr/$10^6$ cells (hJEC-100) JE/MCP-1-non-expressing cells secreted 10–30 U/24 hr/$10^6$ cells. The increased MCA secreted by murine JE/MCP-1 expressing lines is due to increased JE/MCP-1 protein in the medium, not to higher specific activity. Murine JE/MCP-1 appears to be more stable than human JE/MCP-1 in culture, perhaps due to its more extensive glycosylation. (Rollins, B. J., et al. *Mol. Cell. Biol.* 2:4687–4695 (1989)).

By several criteria, JE/MCP-1 expression did not alter the transformed phenotype of CHO cells in vitro. Table I shows that while doubling times of each of the independently derived cell lines varied considerably, the average doubling time of all the JE/MCP-1-expressing lines (25.1 hrs±5.7 sd) was nearly identical to the average doubling time of the JE/MCP-1-non-expressors (26.4 hrs±5.7 sd). Also, JE/MCP-1 expression did not alter the transformed cellular morphology of the CHO cells. Finally, all cell lines formed colonies in soft agar.

TABLE 1

PROPERTIES OF TRANSFECTED CHINESE HAMSTER OVARY CELL LINES

| Cell Line | JE cDNA | Doubling Time (hours) | Soft Agar Colonies/ 25 mm² | No. Cells Injected | Tumors/ Animal Injected |
|---|---|---|---|---|---|
| JE/MCP-1 Non-expressors | | | | | |
| 0A-2 | None | 24.2 | 91 ± 14.0 | 2 × 10⁷ | 1/1 |
| " | " | " | " | 1 × 10⁷ | 2/2 |
| " | " | " | " | 2 × 10⁶ | 3/4 |
| 0A-10 | None | 20.4 | 32 ± 1.9 | 1 × 10⁷ | 2/2 |
| 0B-2 | None | 19.0 | 73 ± 2.6 | 1 × 10⁷ | 0/4 |
| 1A-2 | Antisense | 30.7 | 75 ± 14.5 | 8 × 10⁶ | 2/2 |
| 1B-2 | Antisense | 31.2 | 74 ± 1.7 | 1 × 10⁷ | 1/2 |
| JE/MCP-1 Expressors | | | | | |
| 10A-2 | Murine | 28.8 | 72 ± 7.3 | 2 × 10⁷ | 0/1 |
| " | " | " | " | 1 × 10⁷ | 0/2 |
| " | " | " | " | 2 × 10⁶ | 0/4 |
| 10B-2 | Murine | 17.8 | 86 ± 5.1 | 1 × 10⁷ | 0/2 |
| 10A-10 | Murine | 30.0 | 129 ± 6.8 | 1 × 10⁷ | 0/2 |
| hJEC-10 | Human | 28.8 | 32 ± 6.8 | 1 × 10⁷ | 0/2 |

In vivo, however, JE/MCP-1 expression led to a striking difference in behavior. Table 1 shows that all but one (0B-2) of the JE/MCP-1-non-expressing cell lines formed large subcutaneous tumors that appeared within three weeks of injection into nude mice. In contrast, all of the JE/MCP-1-expressing lines, including the human JE/MCP-1 expressing lines, formed no tumors for as long as ten months after injection. At autopsy, there was no microscopic evidence of residual tumor in the animals that received JE/MCP-1-expressing cells.

Figure 2A:
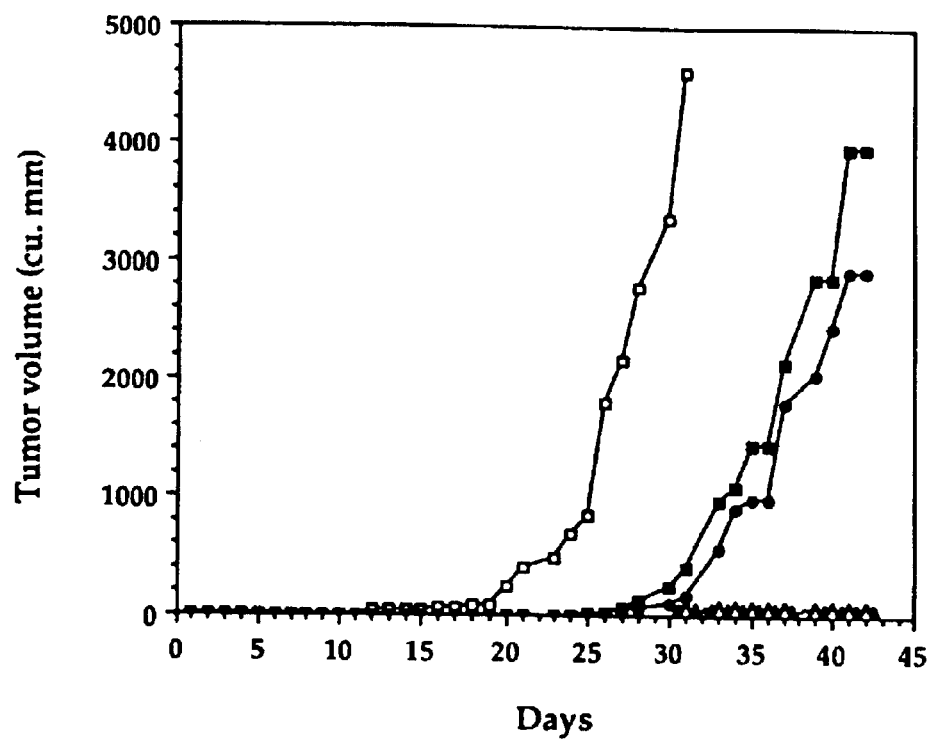
FIGS. 2A and 2B are graphs plotting the growth rate of tumors. Each symbol represents a different mouse. 2A. CHO cells only, $10^7$ 0A-2 cells (open square); $10^7$ 0A-2 cells plus $10^7$ hJEC-10 cells (closed square and closed circle); $10^7$ 0A-2 cells and $10^7$ 10A-10 cells (closed triangle and open triangle); (identical results were obtained with $10^7$ 0A-2 cells and $10^7$ hJEC-100 cells). 2B. CHO and HeLa cells, $10^5$ HeLa cells and $10^7$ 0A-2 cells (open square and open circle); $10^5$ HeLa cells and 1 hJEC-10 cells (closed square and closed circle); $10^5$ HeLa cells and $10^7$ 10A-10 cells (closed triangle and open triangle); (identical results were obtained with $10^7$ HeLa cells and $10^7$ hJEC-100 cells in 3 out of 4 animals).

These observations suggested the possibility that JE/MCP-1-secreting cells attracted monocytes to the site of tumor cell injection and once there, secreted JE/MCP-1 protein induced monocyte tumoricidal activity. To test this hypothesis, JE/MCP-1-expressing cells were mixed with $10^7$ 0A-2 cells, a number of cells that reproducibly led to tumor formation when injected alone (see Table FIG. 2A shows that co-injection of murine JE/MCP-1-expressing cells (10A-10) with 0A-2 cells completely suppressed tumor formation in two animals. Co-injection of high-level human JE/MCP-1-expressing cells (hJEC-100) with 0A-2 cells also completely suppressed tumor formation. Co-injection of low-level human JE/MCP-1-expressing cells (hJEC-10) suppressed tumor formation for 8–10 days, after which tumors appeared. Presumably hJEC-10 cells exerted a suppressive effect transiently until the proliferating 0A-2 cell mass reached a size that enabled it to escape the effect.

Figure 2B:
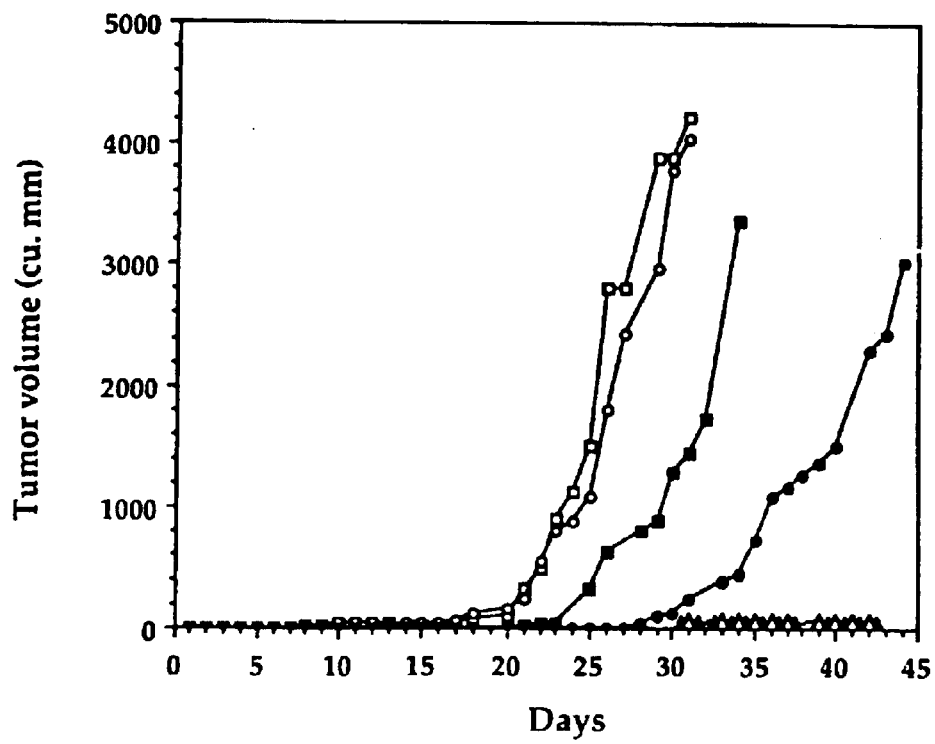

JE/MCP-1-expressors and non-expressors were also co-injected with HeLa cells to test whether JE/MCP-1 expression could suppress tumor formation by another cell type. FIG. 2B shows that 10A-10 cells completely suppressed the formation of tumors by HeLa cells. As above, co-injection with hJEC-10 cells delayed tumor formation. In a separate experiment, 4 of 4 animals injected with $10^7$ HeLa cells formed tumors, while only 1 of 4 animals injected with $10^7$ HeLa cells plus $10^7$ hJEC-100 cells formed tumors. Mice that displayed no tumor growth after receiving HeLa plus hJEC-100 cells were then injected with $10^7$ HeLa cells alone. These mice developed large tumors within 14 days, indicating that prior suppression of HeLa cell tumor growth in the presence of JE/MCP-1 does not render mice immune to rechallenge with HeLa cells.

Histologic examination of the tumors arising from co-injected HeLa and 0A-2 cells revealed a mixture of epithelioid HeLa cells and spindle-shaped CHO cells. Examination of the tumors formed in animals that received HeLa and hJEC-10 cells also demonstrated a mixture of HeLa cells and CHO cells. The presence of some hJEC-10 cells in these tumors was confirmed by Northern blot analysis in which expression of human JE mRNA could be detected. After reaching a certain size, these tumors may overwhelm the host response elicited by the low levels of human JE/MCP-1 secreted by hJEC-10 cells. However, tumor growth still requires the presence of a malignant JE/MCP-1-non-expressing cell line, since hJEC-10 cells injected by themselves cannot form tumors (Table I This suggests again that the intrinsic growth properties of the CHO cells have not been altered by JE/MCP-1 expression, and that the human JE/MCP-1 expressors will proliferate in vivo if they are protected by an enlarging mass of malignant cells.

Figure 3A:
FIGS. 3A, 3B and 3C are photographs (magnification 400X) of hematoxylin and eosin-stained cellular infiltrate elicited by FIG. 3A. 0A-10, FIG. 3B. 10A-10 or FIG. 3C. hJEC-10 cells.
Figure 3B:
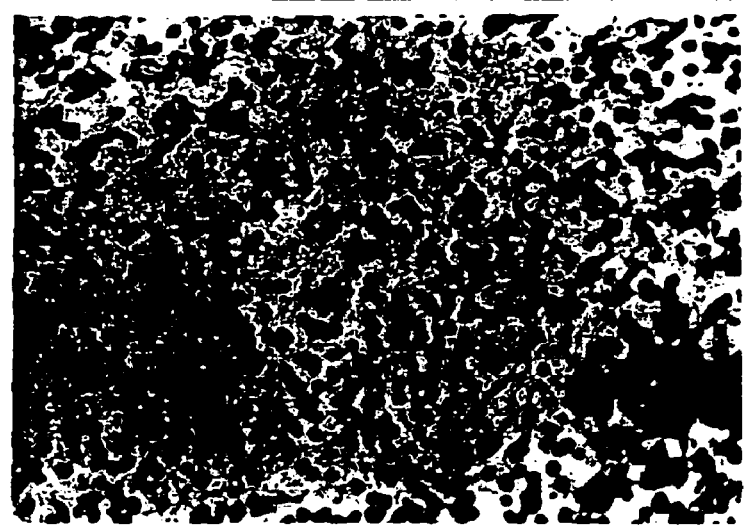
Figure 3C:
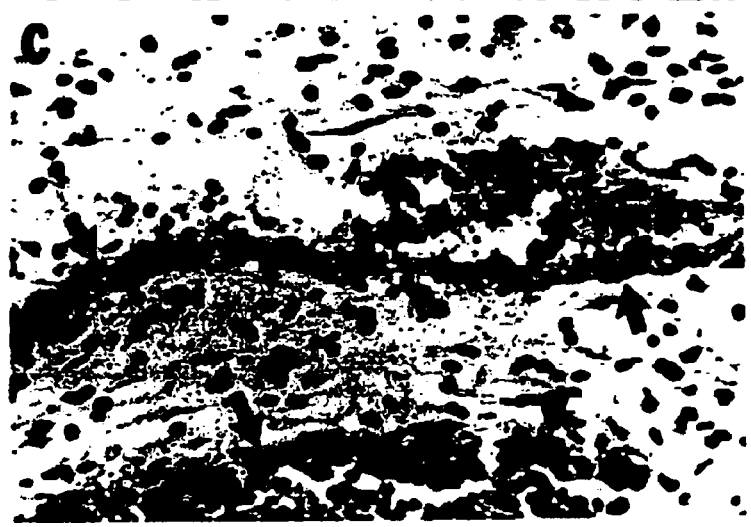
Figure 4A:
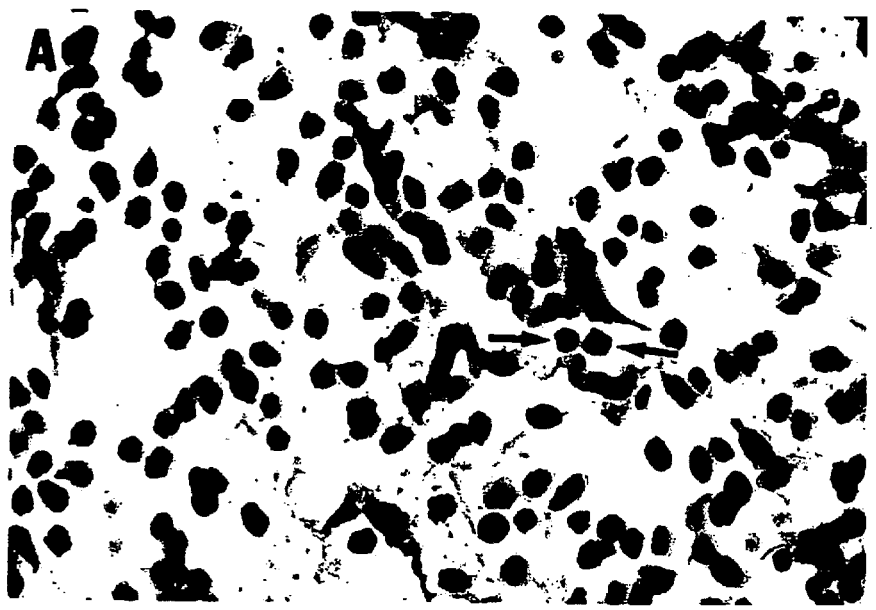
FIGS. 4A and 4B are photographs (magnification 800X) of hematoxylin and eosin-stained cellular infiltrate elicited by hJEC-10 cells.
Figure 4B:

FIGS. 3 and 4 show the results of a histological examination of the sites of CHO cell inoculation 24 hours after cells were injected. JE/MCP-1-non-expressors (darkly stained, large cells indicated by arrows in FIG. 3A) induce the appearance in the underlying connective tissue of only a few cells, most of which are neutrophils. In contrast, CHO cells expressing murine JE/MCP-1 (indicated by arrows in FIG. 3B) elicited an abundant cellular infiltrate. At higher power (FIG. 4A), it is apparent that this infiltrate consisted primarily of monocytes with a reproducibly significant proportion of eosinophils (arrows), usually 10–20%. As might be expected, low-level human JE/MCP-1-expressing cells (hJEC-10) induced a qualitatively similar infiltrate (FIG. 4B) that was intermediate in intensity between the non-expressors and the murine JE/MCP-1 expressors (compare FIG. 3C to FIGS. 3A and 3B).

The results represented by FIGS. 3 and 4 demonstrate a predominantly monocytic infiltrate at the site of tumor cell injection, suggesting that monocytes mediate tumor growth suppression. The effect is probably not mediated by T lymphocytes or by natural killer cells, since purified recombinant JE/MCP-1 has no stimulatory effect on natural killer cells in vitro.

If monocytes are responsible for tumor suppression, there are several possible mechanisms whereby JE/MCP-1-activated monocytes might exert their effects. JE/MCP-1 could induce the expression of a soluble mediator of tumor cells lysis such as tumor necrosis factor (TNF). L. J. Old, *Science*, 230:630–632 (1985). J. L. Urban et al., *Proc. Natl. Acad. Sci. USA* 83:5233–5237 (1986). Alternatively TNF could be expressed and displayed in an active form on the cell surface of activated monocytes. M. Kriegler, et al., *Cell* 53:45–52 (1988).

Interestingly, an eosinophilic component to the inflammatory cell infiltrate was also observed. This may be either a direct effect of JE/MCP-1 or, JE/MCP-1 may induce the expression of another factor with eosinophil chemoattractant properties.

These results point to a clinical role for infused JE/MCP-1 in vertebrate animals, such as humans. For example, JE/MCP-1 can be administered to patients with cancer. This would necessarily be limited to patients with low tumor loads, i.e. as an adjuvant to surgery or cytotoxic chemotherapy. Systemically infused JE/MCP-1 would lead to a generalized increase in the activation state of a vertebrate's monocytes. There is some evidence that patients harboring malignancies have depressed monocyte function. W. G. Chaney et al., *Cell molec. Genet*, 5:15–27 (1986). E. S. Kleinerman et al., Lancet ii: 1102–1105, (1980). If the defect were cytokine based, rather than an inherent monocyte defect, JE/MCP-1 infusion would correct the abnormality.

Alternatively, JE/MCP-1 may prove useful in treating localized complications of malignancy, such as pleural effusions or ascites. Instilling JE/MCP-1 into the involved anatomic space (e.g. the space between the lung and the pleural membrane or the space between the stomach and the peritoneum) can lead to local monocyte accumulation and activation.

As a therapeutic, JE/MCP-1 can be administered to vertebrate animals (i.e. animals having an immune system), including humans. The compounds of this invention can be employed in admixture with conventional excipients, i.e., pharmaceutically acceptable organic or inorganic carrier substances suitable for parental or topical application.

Suitable pharmaceutical carriers include, but are not limited to water, salt solutions, alcohols, polyethylene glycols, gelatin, carbohydrates such as lactose, amylose or starch, magnesium stearate, talc, silicic acid, viscous paraffin, perfume oil, fatty acid esters, hydroxymethylcellulose, polyvinyl pyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., enzyme inhibitors, to further reduce metabolic degradation.

For parenteral application, particularly suitable are injectable, sterile solutions, preferably oily or aqueous solutions, as well as suspensions, emulsions, or implants, including suppositories. Ampoules are convenient unit dosages.

For topical application, there are employed as nonsprayable forms, viscous to semi-solid or solid forms comprising a carrier compatible with topical application and having a dynamic viscosity preferably greater than water. Suitable formulations include but were not limited to solutions, suspensions, emulsions, creams, ointments, powders, liniments, salves, aerosols, etc., which are, if desired, sterilized or mixed with auxiliary agents, (e.g., preservatives, stabilizers, wetting agents, buffers of salts for influencing osmotic pressure, etc.). For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a Freon.

It will be appreciated that the actual preferred amounts of JE/MCP-1 in a specific case will vary according to the specific compound being utilized, the particular compositions formulated, the mode of application, and the particular situs and organism being treated. Dosages for a given host can be determined using conventional considerations, (e.g., by means of an appropriate, conventional pharmacological protocol.).

JE/MCP-1 may also be administered using gene therapy techniques. A number of methods are currently available for introducing and expressing JE/MCP-1 in mammalian cells. Some of these techniques involve removing target cells from a host organism, introducing the gene encoding JE/MCP-1 into target cells, then returning the cells to a host. Additional methods include introducing the gene encoding JE/MCP-1 into target cells in vivo, thereby eliminating the need to remove and further manipulate the target cells In one example of a gene therapy application for JE/MCP-1, tumor killing cells, such as tumor infiltrating lymphocytes (TIL cells) could be genetically engineered to express the JE/MCP-1 protein. Tumor killing cells engineered in this way can provide synergistic local tumor cell killing. The tumor killing cells could be engineered in vitro to express JE/MCP-1 and administered to the vertebrate, or the vertebrate's own supply of tumor killing cells could be engineered in vivo to express JE/MCP-1.

In the alternative, any cell type which localizes to, or can be made to localize to a site of tumor formation can be genetically engineered to express JE/MCP-1 protein, and used for gene therapy. Cells can be engineered in vivo, at the site of tumor formation, or they can be engineered in vitro and subsequently administered to a vertebrate where they will express JE/MCP-1 at the site of tumor formation. Known gene transfer techniques which can be used to engineer cells to express JE/MCP-1 include: vector mediated gene transfer, microinjection, calcium phosphate precipitation, liposome fusion, receptor mediated gene transfer, microprojectile bombardment or polybrene precipitation.

Vector mediated transduction (gene transfer), for example, can be accomplished by any of several known techniques. For example, amphotropic retroviruses are capable of infecting human cells without subsequent replication. these viruses can be made to contain a gene encoding JE/MCP-1 and any desired transcriptional control sequences (in addition to any viral transcriptional control sequences present). After infection, the viral DNA and its insert DNA encoding JE/MCP-1 would integrate into the host cell DNA. Once integrated, either viral transcriptional control elements, or other control elements included in the viral construct, would direct transcription of the gene encoding JE/MCP-1.

Alternatively, for example, adenovirus, a DNA virus, can be used as a vector for DNA encoding JE/MCP-1. Adenovirus will infect nearly all human cells of epithelial origin and its DNA will integrate into a host cell's genomic DNA. Unlike retroviruses, which integrate into many sites in a host genome, adenovirus DNA will integrate at one or two specific sites. This characteristic makes adenovirus vectors less likely than retrovirus vectors to inadvertantly activate host genes. As for retrovirus vectors, JE/MCP-1 DNA can be inserted into adenovirus DNA under the control of either a JE/MCP-1 promoter, or another promoter. Cells infected with the. adenovirus vector construct will express JE/MCP-1.

Tumor cell targets for gene therapy can be infected in vivo by injecting a small volume of retrovirus- or adenovirus-containing solution into the tumor. In the alternative, tumor tissue, e.g., malignant cells from a pleural effusion, can be removed from an individual and infected in vitro. The infected cells could then be injected into an individual where they would express JE/MCP-1 protein.

A more detailed discussion of gene therapy and related techniques are included in the following references which are herein incorporated by reference: "Human Gene Therapy Comes of Age," A. D. Miller, *Nature* 357:455–460 (1992), which describes the current state of the art of gene therapy, with particular emphasis on the human gene therapy approval process, approved human gene marking trials, approved gene therapy trials, gene transfer vectors, target tissues and potential disease targets; and, "Current Protocols in Molecular Biology" edited by F. M. Ausubel et al. Sections 9.0.1, et. seq. describe in detail methods for introduction of DNA into mammalian cells, including transfection and transduction (i.e., introduction of DNA using viral vectors).

The present invention will now be illustrated by the following examples, which are not intended to be limiting in any way.

EXAMPLE 1

In Vivo Tumoricidal Effect of JE/MCP-1 Cell Culture

DUKXB-11 cells (Urlaub, G. and L. A. Chasin, *Proc. Natl. Acad. Sci. USA*, 83:5233–5237 (1987)) (dihydrofolate reductase (DHFR) mutant Chinese hamster ovary (CHO) cells) were grown in the alpha modification of minimal essential medium (MEM-$\alpha$) without ribonucleosides and deoxyribonucleosides, supplemented with 10% bovine calf serum and 10 $\mu$g/ml adenosine, deoxyadenosine, and thymidine (MEM-$\alpha$/BCS/ATT). (Kaufman, R. J. et a. *EMBO J.* 6:187–193 (1989)). HeLa cells were grown in Dulbecco's modified Eagle's medium (DMEM) supplemented with 10% heat-inactivated calf serum and antibiotics.

Transfections and Methotrexate (MTX) Selection

DUKXB-11 cells were grown in 10 cm culture dishes as described above. At 60% confluence, medium was removed and replaced with fresh MEM-α/BCS/AAT supplemented with 3 μg/ml polybrene and incubated overnight. (Chaney, W. G. et., *Somat. Cell Molec. Genet.*, 12:237–244, (1986)). The next day, each dish was given 3 ml fresh MEM-α/BCS/AAT with 83 ng/ml plasmid DNA and 10 μg/ml polybrene. Cells were incubated at 37° C. for 6 hours with rocking every 90 minutes. Medium was then removed and replaced with 5 ml fresh MEM-α/BCS/AAT containing 30% DMSO for exactly 4 minutes. Medium was removed, the cells were washed once with MEM-α, and given 10 ml of MEM-α/BCS/AA. Cells were incubated at 37° C. for 48 hours, then trypsinized and re-plated into 4 culture dishes (10 cm) in nucleoside- and deoxynucleoside-free MEM-α supplemented with 10% dialyzed BCS, and refed with this medium every 3 days. Two independent transfections were performed using pXM (Yang et al. Cell 47:3–10 (1986); pXM-JE10 (murine JE cDNA (Rollins, B. J., et al., *Proc. Natl. Acad. Sci. USA* 85:3738–3742 (1988)) in the sense orientation), pXM-JE1 (murine JE cDNA in the antisense orientation), and pXM-hJE34 (human JE cDNA) (Rollins, B. J., et al., *Mol. Cell. Biol.* 9:4687–4695 (1989)). Colonies from each independent transfection that grew in ribonucleoside- and deoxyribonucleoside-free medium were trypsinized and combined. Step-wise selection in increasing concentrations of methotrexate (MTX) was carried out at the following levels: 0.02 μM, 0.1 μM, 0.5 μM, 2.0 μM, 10.0 μM, and 100.0 μM. At each concentration, surviving colonies were trypsinized and pooled.

Protein Analysis

Confluent cell cultures were incubated in methionine-free MEM-a with 2% dialyzed BCS for 45 minutes, then changed to 0.5 ml of the same medium with 500 μCi [$^{35}$S] methionine (DuPont NEN, Boston, Mass.). Cells were incubated at 37° C. for 4 hours after which the medium was collected, made 1 mM in phenylmethylsulfonyl fluoride (PMSF), centrifuged to remove cells and debris, and stored at −700C. Immune precipitations using anti-JE/MCP-1 antiserum were performed (Rollins, B. J., et al., *Mol. Cell. Biol.* 2:4687–4695 (1989)) and the results analyzed by electrophoresis through an SDS-containing 17% polyacrylamide gel.

Soft Agar Colony Formation Assay

Five thousand cells were suspended in MEM-α containing 10% dialyzed BCS, 0.3% agar, and the appropriate concentration of MTX. While still molten, this suspension was distributed on a gelled 4 ml underlayer of ME-α containing 10% dialyzed BCS, 0.60% agar, and the appropriate concentration of MTX in a 60 mm culture dish. Cells were fed with 3 drops of fresh medium every 5 days. After 14 days, colonies consisting of greater than 50 cells were counted.

Monocyte Chemoattractant Activity (MCA)

Confluent monolayers of CHO cells were incubated in serum-free ME-α for 24 hour, after which the medium was centrifuged to remove cells and debris, and the remaining adherent cells were trypsinized and counted. Fresh human peripheral blood mononuclear cells were purified from the blood of volunteer donors by centrifugation on a cushion of Ficoll-Hypaque (Pharmacia, Piscataway, NJ). Cells at the interface were washed twice in Gey's balanced salt solution (GBSS) with 2% BSA, then resuspended at 4×10$^6$ cells/ml in GBSS with 0.2% BSA, and MCA was measured in a 48-well microchamber apparatus. (Falk, W., et al., *J. Immunol. Methods* 33:239–247 (1980)). The concentration of MCA in CHO cell medium was defined as the reciprocal of the dilution showing half-maximal activity. (Yoshimura, T., et al., *J. Exp. Med.* 169:1449 1459 (1989)).

Nude Mouse Injections

Cells were suspended in 0.2 ml PBS and injected subcutaneously into 4-week old male Swiss nu/nu mice. Mice were monitored daily for tumor growth. Tumor volume was derived by multiplying the values of three perpendicular diameters.

Equivalents

Those skilled in the art will recognize or be able to ascertain using no more than routine experimentation, many equivalents to the specific embodiments of the invention describe herein. Such equivalents are intended to be encompassed by the following claims.

What is claimed is:

1. A method of treating a localized side-effect of malignancy in a mammal comprising locally administering to the mammal a therapeutically effective amount mammal cells that have been generally engineered to express JE/monocyte chemoattractant protein-1 when the cells are present in the mammal.

2. The method of claim 1 wherein the side effect is selected from the group consisting of pleural effusions or ascites.

3. A method of combatting a parasitic infection in a mammal comprising administering to the mammal a therapeutically effective amount of mammalian cells that express JE/monocyte chemoattractant protein-1 1 when present in the mammal.

* * * * *

UNITED STATES PATENT AND TRADEMARK OFFICE
CERTIFICATE OF CORRECTION

PATENT NO. : 6,767,535 B1
DATED : July 27, 2004
INVENTOR(S) : Barrett Rollins and Charles Stiles It is certified that error appears in the above-identified patent and that said Letters Patent is hereby corrected as shown below:

Column 10,
Line 39, delete "mammal" and insert -- mammalian --
Line 40, delete "generally" and insert -- genetically --
Line 49, delete "1 when" and insert -- when --

Signed and Sealed this

Sixteenth Day of November, 2004

JON W. DUDAS
*Director of the United States Patent and Trademark Office*